United States Patent
Youn et al.

(10) Patent No.: US 11,634,740 B2
(45) Date of Patent: Apr. 25, 2023

(54) ALLULOSE EPIMERASE VARIANT, METHOD FOR PREPARING THE SAME, AND METHOD FOR PREPARING ALLULOSE USING THE SAME

(71) Applicant: DAESANG CORPORATION, Seoul (KR)

(72) Inventors: Hyung Seop Youn, Gyeonggi-do (KR); Eun Seok Choi, Gyeonggi-do (KR); Ji Ha Lee, Gyeonggi-do (KR); Suok Su Kim, Gyeonggi-do (KR); Seung Woo Cho, Gyeonggi-do (KR); Tae Yong Kim, Seoul (KR); Hak Jun Kim, Gyeonggi-do (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 17/788,620

(22) PCT Filed: Apr. 27, 2021

(86) PCT No.: PCT/KR2021/005276
§ 371 (c)(1),
(2) Date: Jun. 23, 2022

(87) PCT Pub. No.: WO2021/221418
PCT Pub. Date: Nov. 4, 2021

(65) Prior Publication Data
US 2023/0055400 A1    Feb. 23, 2023

(30) Foreign Application Priority Data

Apr. 27, 2020 (KR) ............... 10-2020-0050750

(51) Int. Cl.
| | |
|---|---|
| *C12P 19/02* | (2006.01) |
| *C12P 19/24* | (2006.01) |
| *C12N 9/90* | (2006.01) |
| *C12N 15/52* | (2006.01) |

(52) U.S. Cl.
CPC ................ *C12P 19/02* (2013.01); *C12N 9/90* (2013.01); *C12P 19/24* (2013.01); *C12Y 501/03* (2013.01)

(58) Field of Classification Search
CPC ..................................................... C12Y 501/03
See application file for complete search history.

(56) References Cited

FOREIGN PATENT DOCUMENTS

| | | |
|---|---|---|
| KR | 10-1203856 B1 | 11/2012 |
| KR | 10-1455759 B1 | 10/2014 |
| KR | 10-1473918 B1 | 12/2014 |
| KR | 10-2019-0012243 A | 2/2019 |

OTHER PUBLICATIONS

Zhangliang Zhu, et al., "Redesign of a novel $_D$-allulose 3-epimerase from *Staphylococcus aureus* for thermostability and efficient biocatalytic production of $_D$-allulose", Microbial Cell Factories, 2019, vol. 18, thesis No. 59, pp. 1-10.
International Search Report for PCT/KR2021/005276 dated Jul. 29, 2021 [PCT/ISA/210].
Written Opinion of the International Searching Authority for PCT/KR2021/005276 dated Jul. 29, 2021 [PCT/ISA/237].

*Primary Examiner* — Maryam Monshipouri
(74) *Attorney, Agent, or Firm* — Sughrue Mion, PLLC

(57) ABSTRACT

The present invention provides: a novel allulose epimerase variant in which an amino acid residue present at a specific position of an amino acid sequence of a wild-type D-allulose 3-epimerase derived from *Flavonifractor plautii* is substituted with another amino acid residue; and various uses of the novel allulose epimerase variant. The novel allulose epimerase variant according to the present invention has a higher conversion rate of fructose to allulose compared to that of the wild-type D-allulose 3-epimerase derived from *Flavonifractor plautii*, and has excellent thermal stability especially under high temperature conditions of 60° C. or higher, and thus can prevent contamination during an industrial-scale enzymatic conversion reaction for the mass production of allulose, shorten production time, and reduce production costs.

10 Claims, 1 Drawing Sheet
Specification includes a Sequence Listing.

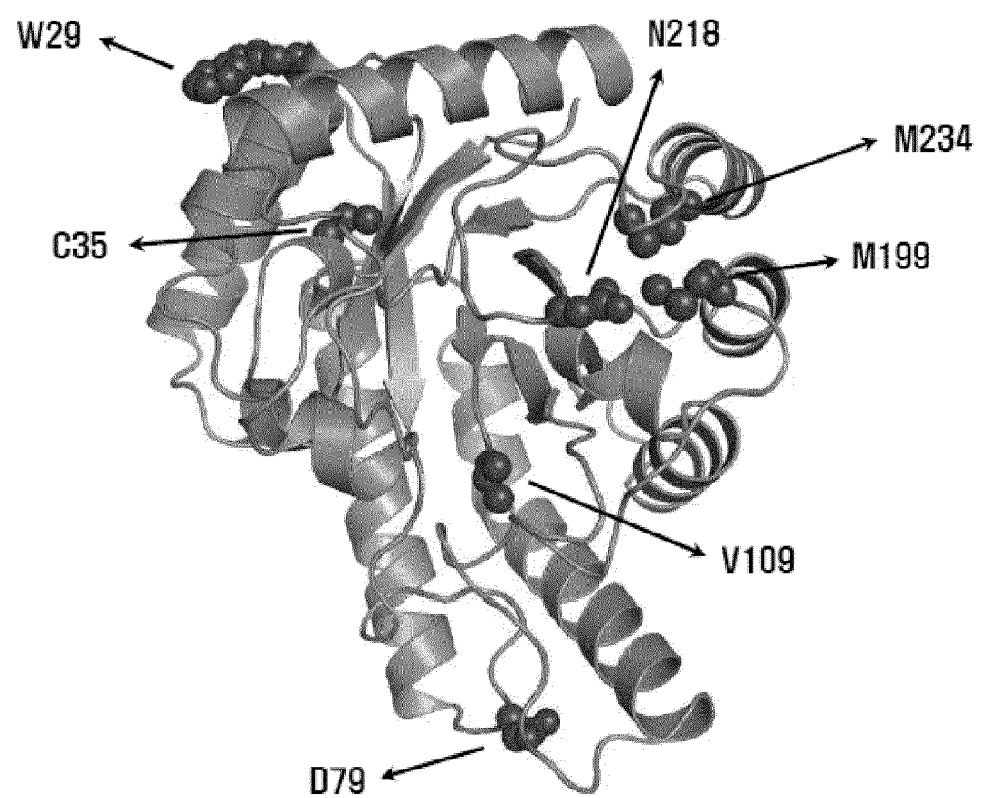

ALLULOSE EPIMERASE VARIANT, METHOD FOR PREPARING THE SAME, AND METHOD FOR PREPARING ALLULOSE USING THE SAME

CROSS REFERENCE TO RELATED APPLICATIONS

This application is a National Stage of International Application No. PCT/KR2021/005276 filed Apr. 27, 2021, claiming priority based on Korean Patent Application No. 10-2020-0050750 filed Apr. 27, 2020, the entire disclosures of which are incorporated herein by reference.

SEQUENCE LISTING

In compliance with the 37 C.F.R. § 1.52(e)(5), the sequence information contained in electronic file name: Sequence Listing As Filed.txt; size: 54.0 KB; and date of creation: Jun. 22, 2022; is hereby incorporated herein by reference in its entirety.

TECHNICAL FIELD

The present invention relates to an allulose epimerase variant, and more particularly, an allulose epimerase variant with improved conversion rate and thermal stability of fructose to allulose compared to D-allulose 3-epimerase derived from *Flavonifractor plautii* and various results derived therefrom.

BACKGROUND ART

D-allulose is an epimer of the third carbon of fructose, which is also called D-psicose. D-allulose has 70% sweetness compared to sugar (Oshima 2006), but only 0.3% energy so that it is a functional monosaccharide that can be applied as a low-calorie sweetener in dietetic foods (Matsuo et al. 2002). Further, D-allulose has the function of absorbing glucose and inhibiting blood sugar so that it can be applied to food products for diabetics, health food products, etc. Since it can suppress the accumulation of abdominal fat through inhibition of enzyme activity involved in lipid synthesis in the liver, it can be used in various functional foods such as health foods (Matsuo et al. 2001; Iida et al. 2008; Hayashi et al. 2010; Hossain et al. 2011).

Due to the above characteristics, allulose is a good source to replace sugar. However, it belongs to rare sugars, which are monosaccharides that are extremely rare in nature. Thus, a method of efficiently preparing allulose is required for application to the food industry. The conventional method of preparing allulose was mainly performed through a chemical process. Billik et al. proposed a method of converting fructose into allulose using the catalytic action of molybdate ions. McDonald produced allulose from 1,2:4,5-di-δ-isopropylidene-beta-D-fructopyranose by a three-step chemical treatment process. Further, Doner produced allulose by heating fructose together with ethanol and trimethylamine. However, although these chemical production methods are expensive, there is a disadvantage in that their efficiency is low, and by-products are significantly generated.

As a biological method of preparing allulose, a method of preparing allulose has been proposed from galactitol, D-tagatose, D-thalitol, or the like using the cellular reaction of microorganisms (Ken Izumori). However, this method is difficult to apply to industrial production since the substrate belongs to rare sugars. The most efficient way for industrialization is to find an enzyme that converts fructose into allulose among the group of D-ketose 3-epimerase. Previously published contents include the production of allulose from fructose using D-tagatose 3-epimerase expressed in the transformed *E. coli* after inserting D-tagatose 3-epimerase derived from *Clostridium cellulolyticum* H (10) (Mu et al. 2011), *Agrobacterium tumefaciens* (Kim et al. 2006), *Pseudomonas cichorii* (Itoh et al. 1994), and *Rhizobium sphaeroides* (Zhang et al. 2009) into *E. coli* and transforming the same.

Regarding the technology for preparing allulose from fructose using an enzyme, Korean Patent Publication No. 10-0744479 discloses a method for preparing allulose using an allulose epimerase derived from *Agrobacterium tumefaciens*. Further, Korean Patent Publication No. 10-0832339 discloses a method of converting fructose into allulose using *Sinorhizobium* YB-58 KCTC 10983BP, which has the activity of converting fructose into allulose. Korea Patent Publication No. 10-1106253 discloses *E. coli* including a polynucleotide encoding the allulose 3-epimerase of *Agrobacterium tumefaciens* C58, which has an activity to catalyze the conversion of fructose into allulose, and a method of preparing allulose from fructose using the same. Korean Patent Publication No. 10-1339443 discloses a ketose 3-epimerase derived from microorganisms belonging to the genus *Rhizobium* and a method of converting fructose to allulose using the same. Korean Patent Publication No. 10-1318422 discloses a D-allulose 3-epimerase derived from *Clostridium scindens* and a method of preparing allulose from fructose using the same. Korean Patent Publication No. 10-1473918 discloses a D-allulose 3-epimerase derived from *Flavonifractor plautii* and a method of preparing allulose from fructose using the same.

However, the wild-type D-allulose 3-epimerase derived from microorganisms does not have a high conversion rate of fructose into allulose and is particularly not suitable for industrialization due to poor thermal stability under optimal conditions of activation temperature. Therefore, there is a need to develop a novel D-allulose 3-epimerase variant with improved conversion rate or thermal stability of fructose to allulose compared to the wild-type D-allulose 3-epimerase derived from microorganisms. Regarding the D-allulose 3-epimerase variant, Korean Patent Laid-Open Publication No. 10-2014-0021974 discloses D-allulose 3-epimerase derived from *Treponema primitia* ZAS-1, which induces mutations at the gene level and shows a fast conversion rate to allulose and stability at high temperatures. Korean Patent Publication No. 10-1203856 discloses an allulose epimerase variant with improved thermal stability obtained by variation of a wild-type allulose epimerase derived from *Agrobacterium tumefaciens*.

DISCLOSURE

Technical Problem

The present invention is derived from the background of the prior art, and the first object of the present invention is to provide a novel D-allulose 3-epimerase variant with the improved conversion rate of fructose to allulose and thermal stability compared to the wild-type D-allulose 3-epimerase derived from *Flavonifractor plautii*.

A second object of the present invention is to provide a method of preparing a novel D-allulose 3-epimerase variant or to provide various elements necessary for preparing a novel D-allulose 3-epimerase variant.

A third object of the present invention is to provide a method of preparing allulose from fructose or to provide various elements necessary for preparing allulose from fructose.

Technical Solution

The applicants of the present invention have applied for a patent, and the invention of preparing wild-type D-allulose 3-epimerase derived from *Flavonifractor plautii* and preparing allulose from fructose using the same has been registered (See Korea Patent Publication No. 10-1473918 (2014.12.11)). The wild-type D-allulose 3-epimerase derived from *Flavonifractor plautii* shows the maximum activity for the conversion of fructose to allulose in a pH range of about 6.5 to 7.0 and a temperature of about 62° C. to 66° C. As the reaction time elapses under the optimum condition of temperature, the enzyme activity rapidly decreases. Thus, its utilization is limited in the industrialization stage for mass production of allulose. Further, since the enzyme conversion reaction for mass production of allulose is generally carried out at high temperatures to prevent contamination, it is necessary to significantly improve thermal stability in order to apply the wild-type D-allulose 3-epimerase derived from *Flavonifractor plautii* to industrialization. The present inventors recognize the inherent issues of wild-type D-allulose 3-epimerase derived from *Flavonifractor plautii*, and utilize protein structure prediction technology to derive amino acid residue position candidates expected to be related to improvement of conversion rate and thermal stability upon change of chemical bond in the amino acid sequence of wild-type D-allulose 3-epimerase and confirm the conversion rate of fructose to allulose and thermal stability were improved when an amino acid residue at a specific position among these is substituted with another amino acid residue, thereby completing the present invention.

In order to achieve the first object, the present invention provides an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13.

In order to achieve the second object, the present invention provides a polynucleotide encoding the allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13. Further, the present invention provides a recombinant vector comprising a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13. Further, the present invention provides a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13, or a recombinant strain transformed by a recombinant vector comprising the polynucleotide. Further, the present invention provides a method for preparing an allulose epimerase variant, the method comprising step of: culturing a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13, or a recombinant strain transformed by a recombinant vector comprising the polynucleotide to express an allulose epimerase variant; and isolating the allulose epimerase variant from a lysate of the recombinant strain expressing the allulose epimerase variant.

In order to achieve the third object, the present invention provides a composition for preparing allulose, the composition comprising the allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13. Further, the present invention provides a composition for preparing allulose, the composition comprising a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13, or a recombinant strain transformed by a recombinant vector comprising the polynucleotide, a culture of the recombinant strain, or a lysate of the recombinant strain. Further, the present invention provides a method for preparing allulose, the method comprising reacting fructose with the allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13 or a composition comprising the allulose epimerase variant. Further, the present invention provides a method for preparing allulose, the method comprising reacting fructose with a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13 or a recombinant strain transformed by a recombinant vector comprising the polynucleotide, a culture of the recombinant strain, a lysate of the recombinant strain, or a composition comprising any one or more thereof.

Advantageous Effects

The novel allulose epimerase variant according to the present invention has a higher conversion activity of fructose to allulose and in particular, excellent thermal stability under high temperature conditions of 60° C. or higher compared to the wild-type D-allulose 3-epimerase derived from *Flavonifractor plautii* so that the enzyme conversion reaction is performed at the industrial level for mass production of allulose to prevent contamination, to shorten production time, and to reduce production cost.

DESCRIPTION OF DRAWINGS

FIG. 1 illustrates the position of a total of seven amino acid residues selected as candidates for substitution to improve the conversion rate of fructose to allulose and thermal stability of D-allulose 3-epimerase derived from *Flavonifractor plautii* by the present inventors.

DETAILED DESCRIPTION OF EMBODIMENT

Hereinafter, the present invention is described in detail.

One aspect of the present invention relates to a novel D-allulose 3-epimerase variant capable of converting fructose to allulose (hereinafter, referred to as "allulose epimerase variant"). The allulose epimerase variant W29K according to one embodiment of the present invention is a wild-type D-allulose 3-epimerase derived from *Flavonifractor plautii* of which tryptophan (Trp), an amino acid residue at position 29 of the amino acid sequence is substituted with lysine (Lys). Further, the allulose epimerase variant W29K/M234I according to one embodiment of the present invention is a wild-type D-allulose 3-epimerase derived from *Flavonifractor plautii* of which tryptophan (Trp), an amino acid residue at position 29 of the amino acid sequence is substituted with lysine (Lys), and methionine (Met), an amino acid residue at position 234 of the amino acid sequence is substituted with isoleucine (Ile) at the same time. Further, the allulose epimerase variant W29K/G216S/M234I according to a more preferred embodiment of the present invention is a wild-type D-allulose 3-epimerase derived from *Flavonifractor plautii* of which tryptophan (Trp), an amino acid residue at position 29 of the amino acid sequence is substituted with lysine (Lys), glycine (Gly), an amino acid residue at position 216 of the amino acid sequence is substituted with serine (Ser), and methionine (Met), an amino acid residue at position 234 of the amino acid sequence is substituted with isoleucine (Ile) at the same time. The allulose epimerase variants W29K, W29K/M234I, and W29K/G216S/M234I according to the present invention have high conversion activity of fructose to allulose and particularly have excellent thermal stability in high temperature conditions of 60° C. or higher compared to wild-type D-allulose 3-epimerase. The allulose epimerase variant may be obtained by a method in which a polynucleotide encoding a wild-type D-allulose 3-epimerase derived from *Flavonifractor plautii* (consisting of the nucleotide sequence represented by SEQ ID NO: 14) is used as a template, PCR is performed using an oligonucleotide having a predetermined nucleotide sequence as a primer pair, then, an overlap extension PCR is performed using the pair of amplified variant fragments as a template and using the oligonucleotide into which the sequence of the restriction enzyme recognition site is introduced as a primer, then a polynucleotide fragment encoding the amino acid sequence of the allulose epimerase variant is inserted into the expression vector to prepare a recombinant expression vector, then the host strain is transformed with the recombinant expression vector to prepare a recombinant strain, and then the recombinant strain is cultured and expressed. The allulose epimerase variant according to the present invention consists of any one amino acid sequence selected from the amino acid sequence represented by SEQ ID NO: 2, the amino acid sequence represented by SEQ ID NO: 11, or the amino acid sequence represented by SEQ ID NO: 13, but the equivalent range of the allulose epimerase variant according to the present invention is not limited thereto. For example, the equivalent range of the allulose epimerase variant according to the present invention includes some amino acids substituted, inserted and/or deleted in the amino acid sequence represented by SEQ ID NO: 2, the amino acid sequence represented by SEQ ID NO: 11 or the amino acid represented by SEQ ID NO: 13 as long as the activity of converting fructose to allulose and thermal stability at a high temperature of 60° C. or higher is maintained. The amino acid substitution is preferably made by conservative amino acid replacement, which does not change the properties of the protein. Further, modification of the amino acid may be performed by glycosylation, acetylation, phosphorylation, or the like. Further, the equivalent range of the allulose epimerase variant according to the present invention may include proteins with increased structural stability against heat, pH, etc. due to mutation or modification in amino acid sequence or increased activity for the conversion of fructose to allulose. Further, the equivalent range of the allulose epimerase variant according to the present invention may include an amino acid sequence having 70% or more, 80% or more, 90% or more, 95% or more, or 99% or more homology with any one amino acid sequence selected from the amino acid sequence represented by SEQ ID NO: 2, the amino acid sequence represented by SEQ ID NO: 11, or the amino acid sequence represented by SEQ ID NO: 13.

Another aspect of the present invention relates to a method for preparing a novel allulose epimerase variant or to various elements required to produce a novel allulose epimerase variant. Various elements necessary to produce the novel allulose epimerase variant include polynucleotides, primer pairs, recombinant vectors, recombinant strains, and the like.

The polynucleotide is a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13, and preferably consisting of any one nucleotide sequence selected from the nucleotide sequence represented by SEQ ID NO: 15, the nucleotide sequence represented by SEQ ID NO: 24, or the nucleotide sequence represented by SEQ ID NO: 26. The term "polynucleotide" as used herein refers to all polyribonucleotides (RNA) or polydeoxyribonucleotides (DNA) that are non-modified or modified. The polynucleotide includes single-stranded or double-stranded DNA, DNA as a mixture of single-stranded and double-stranded regions, single-stranded or double-stranded RNA, RNA as a mixture of single-stranded and double-stranded regions, or hybrid molecules thereof, but are not limited thereto. Further, the equivalent range of the polynucleotide encoding the allulose epimerase variant includes a sequence having substantial homology to any one nucleotide sequence selected from the nucleotide sequence represented by SEQ ID NO: 15, the nucleotide sequence represented by SEQ ID NO: 24, or the nucleotide sequence represented by SEQ ID NO: 26. The substantial homology is determined by aligning any one nucleotide sequence selected from the nucleotide sequence represented by SEQ ID NO: 15, the nucleotide sequence represented by SEQ ID NO: 24, or the nucleotide sequence represented by SEQ ID NO: 26 and any other sequence so as to correspond as much as possible, and analyzing the sequences, and means that any of the other sequences above have 70% or more, 90% or more, or 98% or more sequence homology with any one nucleotide sequence selected from the nucleotide sequence represented by SEQ ID NO: 15, the nucleotide sequence represented by SEQ ID NO: 24, or the nucleotide sequence represented by SEQ ID NO: 26. Those of ordinary skill in the art will readily understand that polynucleotide encoding allulose epimerase variants having the same activity within the range having the substantial homology may be prepared by substituting, adding, or deleting one or more bases of the nucleotide sequence of the polynucleotide using gene recombination techniques, etc. known in the art. Such homology comparison may be performed by calculating the homology between two or more sequences as a percentage (%) using a commercially available computer program.

Further, the primer pair is for synthesizing a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13, and is preferably composed of a forward primer and a reverse primer having the following nucleotide sequence according to the position and type of amino acid residue substitution.

W29K
* Forward primer sequence (5'→3') CCCTGATGGAGAAGCTGGCCAAACTGGGCTTTGACATCTGCGA (SEQ ID NO: 27)
* Reverse primer sequence (5'→3') TCGCAGATGTCAAAGCCCAGTTTGGCCAGCTTCTCCATCAGGG (SEQ ID NO: 28)

G216S
* Forward primer sequence (5'→3') GGCTGGGGCATTTCCACGTGAGCGAGAACAACCGCCGCCCCGC (SEQ ID NO: 29)
* Reverse primer sequence (5'→3') GCGGGGCGGCGGTTGTTCTCGCTCACGTGGAAATGCCCCAGCC (SEQ ID NO: 30)

M234I
* Forward primer sequence (5'→3') ACCGCCTGCCCTGGAAGGACATTGCCGCCGCCCTCAAGCAGGT (SEQ ID NO: 31)
* Reverse primer sequence (5'→3') ACCTGCTTGAGGGCGGCGGCAATGTCCTTCCAGGGCAGGCGGT (SEQ ID NO: 32)

Further, the recombinant vector includes a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13. The recombinant vector may be provided in the form of inserting a polynucleotide encoding an allulose epimerase variant into a cloning vector or an expression vector using a known standard method. The term "cloning vector" used in the present invention is defined as a material capable of carrying and repreparing a DNA fragment into a host cell. In the present invention, the cloning vector may further include a polyadenylation signal, a transcription termination sequence, and a multiple cloning site. In this case, the multiple cloning site includes at least one endonuclease restriction enzyme restriction site. In addition, the cloning vector may further include a promoter. For example, in the present invention, the polynucleotide encoding the allulose epimerase variant may be located upstream of a polyadenylation signal and a transcription termination sequence. In addition, the term "expression vector" used in the present invention is defined as a DNA sequence necessary for transcription and translation of the cloned DNA in a suitable host. Further, the term "expression vector" used in the present invention refers to a genetic construct including essential regulatory elements operably linked to the insert so that the insert is expressed if it is present in the cells of an individual. The expression vector may be produced and purified using standard recombinant DNA techniques. The type of expression vector is not particularly limited as long as it has a function of expressing a desired gene in various host cells of prokaryotic and eukaryotic cells and preparing a desired protein. However, it is preferably a promoter showing powerful activity and a vector capable of preparing a large amount of a foreign protein in a form similar to that of the natural state while having strong expression power. The expression vector preferably contains at least a promoter, a start codon, a gene encoding a desired protein, and a stop codon terminator. In addition, it may appropriately include DNA encoding the signal peptide, additional expression control sequences, untranslated regions on the 5' and 3' sides of the desired gene, a selection marker region, a replicable unit, or the like. The term "promoter" means a minimal sequence sufficient to direct transcription. Further, the promoter may include a promoter configuration sufficient to express a cell type-specific or regulatable promoter-dependent gene induced by an external signal or agent, and these configurations may be located at the 5' or 3' portion of the gene. These promoters include both conservative and inducible promoters. The promoter sequence may be derived from prokaryotes, eukaryotes, or viruses. The term "operably linked" used in the present invention means that one function is regulated by another by polynucleotide sequence association on a single polynucleotide. For example, if the promoter is capable of regulating the expression of the coding sequence (i.e., the coding sequence is under the transcriptional regulation of the promoter), the promoter is linked and operated to the coding sequence, or if the ribosome binding site is positioned to facilitate translation, the ribosome binding site is linked and operated to the coding sequence. The coding sequence may be operated by linking to a regulatory sequence in the sense or antisense direction. The recombinant vector according to the present invention is preferably an expression vector.

Further, the recombinant strain is transformed with a polynucleotide encoding an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13 or a recombinant vector including the polynucleotide. The term "recombinant strain" used in the present invention refers to a cell transformed by introducing a polynucleotide encoding one or more target proteins or an expression vector having the same into a host cell. Methods for preparing transformants by introducing the expression vector into host cells include transient transfection, microinjection, transduction, cell fusion, calcium phosphate precipitation, liposome mediated transfection, DEAE dextran-mediated transfection, polybrene-mediated transfection, electroporation, electroinjection, a chemical treatment method such as PEG, a method using a gene gun, a heat shock method, and the like, but are not limited thereto. The host cells that may be transformed with the expression vector in the present invention are not greatly limited, as long as they are known in the art, such as prokaryotic cells, plant cells, insect cells, and animal cells, and preferably a host having high DNA introduction efficiency and high expression efficiency of the introduced DNA is usually used. For example, the host cell may be *E. coli*. The *E. coli* may include BL21, JM109, K-12, LE392, RR1, DH5a, W3110, or the like, but is not limited thereto. In addition, the host cell may be a strain selected from the group consisting of *Bacillus* sp. strains such as *Bacillus subtilis* and *Bacillus thuringiensis*, *Corynebacterium* sp. strains such as *Corynebacterium glutamicum*, *Salmonella* sp. strains such as *Salmonella typhimurium*, other *Serratia marcescens*, and Enterobacteriaceae strains such as various *Pseudomonas* species.

Further, a method for preparing an allulose epimerase variant, the method comprising step of: culturing the recombinant strain transformed by the polynucleotide encoding the allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13 or the recombinant vector comprising the polynucleotide to express an allulose epimerase variant; and isolating the psicose epimerase from a lysate of the recombinant strain expressing the allulose epimerase variant. Expression of the protein by the host cell may be induced by using lactose, isopropyl-1-thio-β-D-galactopyranoside (IPTG), as an inducing factor, etc., and the induction time may be adjusted to maximize the amount of protein. In the present invention, the allulose epimerase variant may be recovered from the lysate of the recombinant strain. The cells used in protein expression may be lysed by various physical or chemical means such as freeze-thawing repetition, sonication, mechanical breakage, or a cell lytic agent and may be isolated or purified by a general biochemical isolation technique (Sambrook et al., Molecular Cloning: A laboratory Manual, 2nd Ed., Cold Spring Harbor Laboratory Press, 1989; Deuscher, M., Guide to Protein Purification Methods Enzymology, Vol. 182. Academic Press. Inc., San Diego, Calif., 1990). For example, the method of isolating or purifying the protein expressed by the host cell includes electrophoresis, centrifugation, gel filtration, precipitation, dialysis, chromatography (ion exchange chromatography, affinity chromatography, immunosorbent affinity chromatography, reverse-phase HPLC, and gel permeation HPLC), isoelectricity focus, and various modified or complex methods thereof, but is not limited thereto. Meanwhile, in the present invention, the isolating of the allulose epimerase variant from the lysate of the recombinant strain may be preferably performed by affinity chromatography using a peptide tag. As the peptide tag, various known tags such as a HA tag, a FLAG tag, a His tag, a biotin carboxyl carrier protein (BCCP), a c-myc tag, a V5 tag, a glutathione-S-transferase (GST), or a maltose binding protein (MBP) may be used, and among them, the His tag is preferably used. The His-tagging protein is specifically trapped on a column of a nickel-nitrilotriacetic acid (Ni-NTA) resin and may be released by EDTA or imidazole.

Yet another aspect of the present invention relates to a method of preparing allulose from fructose or various elements required for preparing the allulose from the fructose. As various elements required for preparing the allulose from the fructose, there is a composition for preparing the allulose.

An example of the composition for producing the allulose includes an allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13. Further, another example of the composition for producing the allulose includes a recombinant strain which is transformed by the polynucleotide encoding the allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13 or a recombinant vector including the polynucleotide, a culture of the recombinant strain, or a lysate of the recombinant strain. In this case, preferably, the composition for producing the allulose may further include one or more kinds selected from the group consisting of manganese ions, nickel ions, and cobalt ions, and more preferably, may further include nickel ions or cobalt ions. The novel allulose epimerase variant according to the present invention has a metalloenzyme characteristic in which activation is adjusted by a metal ion and performs the reaction by the enzyme in the presence of a specific metal ion such as nickel ions or cobalt ions to increase a production yield of the allulose.

Further, an example of the method of producing the allulose from the fructose includes reacting the fructose with a composition including the recombinant strain which is transformed by the polynucleotide encoding the allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13 or a recombinant vector including the polynucleotide, a culture of the recombinant strain, a lysate of the recombinant strain or a composition including one or more thereof. Further, the method of producing the allulose from the fructose may additionally include adding metal ions, and a kind of metal ion is as described above. As an example, the metal ion may be added to the fructose that is a substrate or added to a mixture of the enzyme variant and the fructose. Further, as another example, the metal ion may be added to a carrier immobilized with the enzyme variant (before adding the fructose), added to a mixture of the carrier immobilized with the enzyme variant and the fructose (after adding the fructose), or added in a form of the mixture with the fructose when the fructose is added. In the case of using the recombinant strain, the metal ion may be added in the culture or the culturing may be performed in a culture medium added with the metal ion. Further, in the method of producing the allulose from the fructose, the allulose epimerase variant or the recombinant strain is preferably immobilized in the carrier. The carrier may create an environment in which the activity of the immobilized enzyme may be maintained for a long amount of time and may be selected from all known carriers which may be used for enzyme immobilization. For example, sodium alginate may be used as the carrier. The sodium alginate is a natural colloidal polysaccharide abundant in the cell walls of algae and consists of β-D-mannuronic acid and α-L-gluronic acid. In terms of the content thereof, the sodium alginate is formed by randomly forming a β-1,4 bond and the strain or the enzyme is stably immobilized, and thus it is advantageous to have excellent allulose yield. As an example, in order to further promote the yield of the allulose, a sodium alginate solution at a concentration of 1.5 to 4.0% (w/v) (for example, an aqueous sodium alginate solution), preferably a sodium alginate solution at a concentration of about 2.5% (w/v) may be used for immobilizing the recombinant strain. Further, in the method of producing the allulose from the fructose, the reaction temperature is in the range of 60° C. to 70° C., preferably 60° C. to 67° C., and more preferably 62° C. to 65° C. when considering the stability and maximum activity of the enzyme variant, and the reaction pH is in the range of 6.5 to 8, preferably 6.5 to 7.5, and more preferably 6.5 to 7. Further, in the method of producing the allulose from the fructose, the concentration of the fructose is not particularly limited thereto, but preferably 1% to 75% (w/w) and more preferably 4 to 35% (w/w) based on the entire reactant when considering productivity or economics. Further, in the method of producing the allulose from the fructose, the concentration of the used enzyme variant may be 0.001 mg/ml to 0.1 mg/ml, preferably 0.01 mg/ml to 0.1 mg/ml, and more preferably 0.02 mg/ml to 0.05 mg/ml based on the entire reactant. Further, in the case of producing the allulose from the fructose by using the recombinant strain, the host strain of the recombinant strain is preferably a cytologically safe strain. The cytologically safe strain means a generally accepted as safe (GRAS) class strain, which is generally accepted as safe and for example, may be selected from a *Saccharomyces* sp., *Bacillus* sp. *Corynebacterium* sp. strain, and the like. These strains are industrial microorganisms which produce chemical materials having various uses in fields of feed, medicines, food products, and the like. These strains have a strain characteristic which is easily used for gene manipulation and mass culture and has high stability under various process conditions. Further, these strains have a relatively hard cell membrane structure as compared with other bacteria to have a biological characteristic in which these strains are present in a stable state even under high osmotic pressure caused by high sugar concentration, etc. The particular examples of the generally accepted as safe (GRAS) class strain include *Saccharomyces cerevisiae, Bacillus subtilis, Corynebacterium glutamicum*, and the like.

Hereinafter, the present invention will be described in more detail by Examples. However, the following Examples are only intended to clearly illustrate the technical features of the present invention and do not limit the protection scope of the present invention.

Example 1: Search for Amino Acid Substitution Positions for Improving Conversion Rate and Thermal Stability of D-Allulose 3-Epimerase In order to improve the conversion rate of fructose to allulose and thermal stability of D-allulose 3-epimerase derived from *Flavonifractor plautii*, amino acid substitution positions were selected based on protein structure prediction. The D-allulose 3-epimerase (or D-psicose 3-epimerase) derived from *Flavonifractor plautii* is disclosed in a Korean registered patent No. 10-1473918 (2014.12.11) previously filed and registered by the applicant of the present invention. The D-allulose 3-epimerase derived from *Flavonifractor plautii* consists of the amino acid sequence represented by SEQ ID NO: 1, has maximum activity for the conversion of fructose to allulose under neutral pH conditions, and is capable of mass-producing allulose from fructose with a high yield in a short time, but there is a problem in that the activity decreases rapidly when the enzyme reaction is carried out under high temperature conditions to prevent contamination, etc. In order to improve the conversion rate of fructose to allulose and thermal stability of D-allulose 3-epimerase derived from *Flavonifractor plautii*, the inventors of the present invention predicted the protein structure using a homology modeling technique based on the amino acid sequence of the D-allulose 3-epimerase derived from *Flavonifractor plautii*, to search for amino acid substitution positions. The homology modeling was performed using a Robetta server, and protein structure prediction and analysis were performed using software programs such as Coot, PyMol, and UCSF Chimera. The three-dimensional structural model analysis of the D-allulose 3-epimerase was performed to select a total of seven amino acid residue positions that are expected to be related to the improvement of the conversion rate and thermal stability when the chemical bond is changed and the amino acid residues to be substituted at the positions. FIG. 1 shows the position of a total of seven amino acid residues selected as candidates for substitution to improve the conversion rate of fructose to allulose and thermal stability of D-allulose 3-epimerase derived from *Flavonifractor plautii* by the inventors of the present invention. In FIG. 1, "W29" represents tryptophan (Trp) at position 29 of the amino acid sequence represented by SEQ ID NO: 1, "C35" represents cysteine (Cys) at position 35 of the amino acid sequence represented by SEQ ID NO: 1, "D79" represents aspartic acid (Asp) at position 79 of the amino acid sequence represented by SEQ ID NO: 1, "V109" represents valine (Val) at position 109 in the amino acid sequence represented by SEQ ID NO: 1, "M199" represents methionine (Met) at position 199 in the amino acid sequence represented by SEQ ID NO: 1, "N218" represents asparagine (Asn) at position 218 in the amino acid sequence represented by SEQ ID NO: 1, and "M234" represents methionine (Met) present at position 234 in the amino acid sequence represented by SEQ ID NO: 1. In addition, although not shown in FIG. 1, from the results of previous studies, glycine (Gly) present at the position 216 among the amino acid sequence represented by SEQ ID NO: 1 was named "G216" and selected as a substitution candidate. In addition, as described below, the enzyme variant W29K consisting of the amino acid sequence represented by SEQ ID NO: 2 was prepared by substituting lysine (Lys) for tryptophan (Trp) present at the position 29 of the amino acid sequence represented by SEQ ID NO: 1. The enzyme variant C35L consisting of the amino acid sequence represented by SEQ ID NO: 3 was prepared by substituting leucine (Leu) for cysteine (Cys) present at the position 35 of the amino acid sequence represented by SEQ ID NO: 1. The enzyme variant D79P consisting of the amino acid sequence represented by SEQ ID NO: 4 was prepared by substituting proline (Pro) for aspartic acid (Asp) present at the position 79 of the amino acid sequence represented by SEQ ID NO: 1. The enzyme variant V109A consisting of the amino acid sequence represented by SEQ ID NO: 5 was prepared by substituting alanine (Ala) for valine (Val) present at the position 109 of the amino acid sequence represented by SEQ ID NO: 1. The enzyme variant M199F consisting of the amino acid sequence represented by SEQ ID NO: 6 was prepared by substituting phenylalanine (Phe) for methionine (Met) present at the position 199 of the amino acid sequence represented by SEQ ID NO: 1. The enzyme variant G216S consisting of the amino acid sequence represented by SEQ ID NO: 7 was prepared by substituting serine (Ser) for glycine (Gly) at position 216 of the amino acid sequence represented by SEQ ID NO: 1. The enzyme variant N218C consisting of the amino acid sequence represented by SEQ ID NO: 8 was prepared by substituting cysteine (Cys) for asparagine (Asn) at position 218 in the amino acid sequence represented by SEQ ID NO: 1. The enzyme variant M234I consisting of the amino acid sequence represented by SEQ ID NO: 9 was prepared by substituting isoleucine (Ile) for methionine (Met) at position 234 in the amino acid sequence represented by SEQ ID NO: 1. Further, the enzyme variant W29K/G216S consisting of the amino acid sequence represented by SEQ ID NO: 10 was prepared by substituting lysine (Lys) for tryptophan (Trp) present at the position 29 of the amino acid sequence represented by SEQ ID NO: 1 and substituting serine (Ser) for glycine (Gly) at position 216 of the amino acid sequence represented by SEQ ID NO: 1 at the same time. The enzyme variant W29K/M234I consisting of the amino acid sequence represented by SEQ ID NO: 11 was prepared by substituting lysine (Lys) for tryptophan (Trp) present at the position 29 of the amino acid sequence represented by SEQ ID NO: 1 and substituting isoleucine (Ile) for methionine (Met) at position 234 in the amino acid sequence represented by SEQ ID NO: 1 at the same time. The enzyme variant G216S/M234I consisting of the amino acid sequence represented by SEQ ID NO: 12 was prepared by substituting serine (Ser) for glycine (Gly) at position 216 of the amino acid sequence represented by SEQ ID NO: 1 and substituting isoleucine (Ile) for methionine (Met) at position 234 in the amino acid sequence represented by SEQ ID NO: 1 at the same time. Further, the enzyme variant W29K/G216S/M234I consisting of the amino acid sequence represented by SEQ ID NO: 13 was prepared by substituting lysine (Lys) for tryptophan (Trp) present at the position 29 of the amino acid sequence represented by SEQ ID NO: 1, substituting serine (Ser) for glycine (Gly) at position 216 of the amino acid sequence represented by SEQ ID NO: 1 and substituting isoleucine (Ile) for methionine (Met) at position 234 in the amino acid sequence represented by SEQ ID NO: 1 at the same time.

Example 2: Preparation of Recombinant Vector and Recombinant Strain for Overexpression of D-Allulose 3-Epimerase Variant Derived from *Flavonifractor plautii*

The fragments of polynucleotide encoding the amino acid sequence of twelve enzyme variants (W29K, C35L, D79P, V109A, M199F, G216S, N218C, M234I, W29K/G216S, W29K/M234I, G216S/M234I, and W29K/G216S/M234I) were produced using the overlap extension polymerase chain reaction method based on the wild-type polynucleotide of the allulose epimerase derived from *Flavonifractor plautii*.

First, a PCR reaction was performed using the primers shown in Table 1 below in order to prepare a gene encoding an allulose epimerase variant derived from *Flavonifractor plautii*. Specifically, 1 pM of the oligonucleotide as a primer in Table 1 and 100 ng of wild-type polynucleotide (SEQ ID NO: 14) of allulose epimerase variant derived from *Flavonifractor plautii* used as a template were mixed to the reaction solution to which 100 μM of deoxynucleotide triphosphate (dATP, dCTP, dGTP, dTTP) was added. PCR reaction was then performed in 25 cycles to 30 cycles in the presence of 1 unit of pfu-X DNA polymerase mixture (Binoneer) using a Thermocycler (TP600, TAKARA BIO Inc., JAPAN).

TABLE 1

| Primer Description | Primer sequence (5'→3') |
| --- | --- |
| W29K forward primer | CCCTGATGGAGAAGCTGGCCAAACTGGG CTTTGACATCTGCGA (SEQ ID NO: 27) |
| W29K reverse primer | TCGCAGATGTCAAAGCCCAGTTTGGCCA GCTTCTCCATCAGGG (SEQ ID NO: 28) |
| C35L forward primer | CCTGGCTGGGCTTTGACATCCTGGAGGT GGCCTCCGCCGAGTG (SEQ ID NO: 33) |
| C35L reverse primer | CACTCGGCGGAGGCCACCTCCAGGATGT CAAAGCCCAGCCAGG (SEQ ID NO: 34) |
| D79P forward primer | CCAAATACGACCTGGCCAGCCCCGATCC GGCGGTGCGGGAGAA (SEQ ID NO: 35) |
| D79P reverse primer | TTCTCCCGCACCGCCGGATCGGGGCTGG CCAGGTCGTATTTGG (SEQ ID NO: 36) |
| V109A forward primer | GGGCGGCCATCCTCAACGGCGCCTCCTA CGCCGGGTGGCAGGC (SEQ ID NO: 37) |
| V109A reverse primer | GCCTGCCACCCGGCGTAGGAGGCGCCGT TGAGGATGGCCGCCC (SEQ ID NO: 38) |
| M199F forward primer | TGAACATCGAGGAGGACAGCTTCGTGGA CGCCATTCTGGAGGC (SEQ ID NO: 39) |
| M199F reverse primer | GCCTCCAGAATGGCCGTCCACGAAGCTGT CCTCCTCGATGTTCA (SEQ ID NO: 40) |
| G216S forward primer | GGCTGGGGCATTTCCACGTGAGCGAGAA CAACCGCCGCCCCGC (SEQ ID NO: 29) |
| G216S reverse primer | GCGGGGCGGCGGTTGTTCTCGCTCACGT GGAAATGCCCCAGCC (SEQ ID NO: 30) |
| N218C forward primer | GGCATTTCCACGTGGGGGAGTGCAACCG CCGCCCCGCCGGCTC (SEQ ID NO: 41) |
| N218C reverse primer | GAGCCGGCGGGGCGGCGGTTGCACTCCC CACGTGGAAATGCC (SEQ ID NO: 42) |

TABLE 1-continued

| Primer Description | Primer sequence (5'→3') |
| --- | --- |
| M234I forward primer | ACCGCCTGCCCTGGAAGGACATTGCCGC CGCCCTCAAGCAGGT (SEQ ID NO: 31) |
| M234I reverse primer | ACCTGCTTGAGGGCGGCGGCAATGTCCT TCCAGGGCAGGCGGT (SEQ ID NO: 32) |

After amplifying the variant fragments through primer combination, the overlap extension PCR was performed using each pair as a template and using an oligonucleotide into which the sequence of the NdeI and XhoI restriction enzyme recognition sites was introduced as a primer to finally produce polynucleotide fragments encoding the amino acid sequence of twelve enzyme variants (W29K, C35L, D79P, V109A, M199F, G216S, N218C, M234I, W29K/G216S, W29K/M234I, G216S/M234I, and W29K/G216S/M234I). Table 2 below shows the nucleotide sequence of the primers used to introduce the sequence of the restriction enzyme recognition site.

TABLE 2

| Primer Description | Primer sequence (5'→3') |
| --- | --- |
| NdeI forward primer | GCATGCCATATGAACCCGATTGGAATGCA |
| NdeI reverse primer | GCATGCCTCGAGCGCGGTCAGCTCCTTGAGGA |

The nucleotide sequence represented by SEQ ID NO: 15 represents a polynucleotide fragment encoding the amino acid sequence of the enzyme variant W29K, the nucleotide sequence represented by SEQ ID NO: 16 represents a polynucleotide fragment encoding the amino acid sequence of the enzyme variant C35L, the nucleotide sequence represented by SEQ ID NO: 17 represents the polynucleotide fragment encoding the amino acid sequence of the enzyme variant D79P, the nucleotide sequence represented by SEQ ID NO: 18 represents the polynucleotide fragment encoding the amino acid sequence of the enzyme variant V109A, the nucleotide sequence represented by SEQ ID NO: 19 represents the polynucleotide fragment encoding the amino acid sequence of the enzyme variant M199F, the nucleotide sequence represented by SEQ ID NO: 20 represents the polynucleotide fragment encoding the amino acid sequence of the enzyme variant G216S, the nucleotide sequence represented by SEQ ID NO: 21 represents the polynucleotide fragment encoding the amino acid sequence of the enzyme variant N218C, the nucleotide sequence represented by SEQ ID NO: 22 represents the polynucleotide fragment encoding the amino acid sequence of the enzyme variant M234I, the nucleotide sequence represented by SEQ ID NO: 23 represents the polynucleotide fragment encoding the amino acid sequence of the enzyme variant W29K/G216S, the nucleotide sequence represented by SEQ ID NO: 24 represents the polynucleotide fragment encoding the amino acid sequence of the enzyme variant W29K/M234I, the nucleotide sequence represented by SEQ ID NO: 25 represents the polynucleotide fragment encoding the amino acid sequence of the enzyme variant G216S/M234I, and the nucleotide sequence represented by SEQ ID NO: 26 represents the polynucleotide fragment encoding the amino acid sequence of the enzyme variant W29K/G216S/M234I. The nucleotide sequences represented by SEQ ID NOs: 15 to 26 consist of nucleotide sequences that directly correspond to the amino acid sequence of the enzyme variant, and the sequence of the restriction enzyme recognition site was excluded for convenience.

Thereafter, the prepared polynucleotide fragments were inserted into the same restriction enzyme site of the expression vector pET28a (Novagen) using restriction enzymes NdeI and XhoI to prepare twelve types of recombinant expression vectors. In addition, a heat shock method (See Sambrook and Russell: Molecular Cloning.) was used to introduce a recombinant expression vector into *E. coli* BL21 (DE3) (Invitrogen) to transform, thereby producing twelve recombinant *E. coli*. A 60% glycerin solution was added to the produced recombinant *E. coli* and stored frozen at −70° C. before culturing for enzyme expression.

Example 3: Expression and Purification of D-Allulose 3-Epimerase Variant Derived from *Flavonifractor plautii*

1 ml of recombinant *E. coli* prepared in Example 2 was inoculated into a 1 L flask containing 150 ml of protein expression medium having the composition of the following Table 3 (based on 1 L of medium), and they were cultured with a shaking incubator for 24 hours while maintaining the temperature condition of 32° C. and the shaking condition of 140 rpm. Overexpression of the allulose epimerase variant was induced with 1% lactose contained in the medium.

TABLE 3

| Medium component | Amount | Medium component | Amout |
|---|---|---|---|
| Glycerol | 9.0 weight % | MgSO$_4$ | 0.1 weight % |
| Lactose | 1.0 weight % | FeSO$_4$ | 10.0 ppm |
| (NH$_4$)$_2$SO$_4$ | 0.6 weight % | MnSO$_4$ | 10.0 ppm |
| KH$_2$PO$_4$ | 0.5 weight % | ZnSO$_4$ | 10.0 ppm |
| YPA | 1.5 weight % | antifoaming agent (Neorin) | 1.0 drop |

Thereafter, the overexpressed allulose epimerase variant was isolated by the following method. First, the culture solution of the recombinant *E. coli* was centrifuged at 4100×g and 4° C. for about 15 minutes to remove the supernatant, and the strain cells of the recombinant *E. coli* were recovered. Then, the recovered strain cells of recombinant *E. coli* cells were suspended in a lysis buffer (containing 50 mM potassium phosphate monobasic, 300 mM potassium chloride, and 5 mM imidazole) and treated with an ultrasonic disruptor (sonicator) to disrupt the cells. Thereafter, the cell lysate was centrifuged at 15,814×g and 4° C. for about 10 minutes to remove the cell pellet, and only the supernatant was recovered. Then, a purified enzyme solution containing an allulose epimerase variant was separated from the supernatant recovered using a histidine tag (His-tag) affinity chromatography column and a desalting column.

Example 4: Confirmation of Conversion Rate of Fructose to Allulose and Thermal Stability of d-Allulose 3-Epimerase Variant In order to confirm the conversion rate of fructose to allulose and thermal stability of the wild-type and variant of the allulose epimerase derived from *Flavonifractor plautii*, the enzyme was exposed to high temperature for a certain period of time, and then the degree to which the conversion activity of fructose to allulose decreases was analyzed. Specifically, the purified enzyme solution (enzyme concentration 1 mg/ml) obtained in Example 3 was stored and heated in a constant temperature water bath at 62° C. for 0 hours, 1 hour, and 2 hours. Then, the heat-treated purified enzyme solution was added to a 50 mM PIPES buffer solution (pH 7.0) containing 4% (w/w) fructose and metal ions of 1 mM nickel sulfate (NiSO4) so that the enzyme concentration became 25 μg/ml. They were reacted for 25 minutes in a temperature condition of 65° C. and a shaking condition of 120 rpm using a shaking constant temperature water bath (VS-1205SW1, Vision Science). Thereafter, the temperature of the reaction product was lowered to 4° C. to stop the reaction, and the supernatant was recovered by centrifugation under conditions of 16,600×g and 4° C. Then, the allulose concentration and fructose concentration in the supernatant were measured using a high-performance liquid chromatography (HPLC) system (SP930D pump, Youngrin equipment; MIDAS automatic sample injector, Spark Holland) equipped with a sugar analysis column (Benson, USA) and a refractive index detector (2414 refractive index detector, Waters). The conversion rate of fructose to allulose was calculated from the measured results, and the conversion rate was used as an index of enzyme activity.

Tables 4 and 5 below show the conversion rate of fructose to allulose according to heat treatment conditions when the wild-type and variant of the allulose epimerase derived from *Flavonifractor plautii* were heat-treated.

TABLE 4

| Heat treatment time at 62° C. | Conversion rate (%) of fructose to allulose according to heat treatment time for wild-type and variant of allulose epimerase | | | | | | |
|---|---|---|---|---|---|---|---|
| | Wild-type | W29K | C35L | D79P | V109A | M199F | G21GS |
| 0 hour | 17.8 | 20.9 | 16.3 | 18.1 | 1.0 | 16.4 | 17.6 |
| 1 hour | 4.9 | 9.4 | 1.8 | 0.4 | 0.1 | 2.6 | 12.4 |
| 2 hours | 2.4 | 5.3 | 0.0 | 0.3 | 0.0 | 0.7 | 7.7 |

TABLE 5

| Heat treatment time at 62° C. | Conversion rate (%) of fructose to allulose according to heat treatment time for wild-type and variant of allulose epimerase | | | | | |
|---|---|---|---|---|---|---|
| | N218C | M234I | W29K/G216S | W29K/M234I | G216S/M234I | W29K/G216G/M234I |
| 0 hr | 14.3 | 19.5 | 21.6 | 22.3 | 20.7 | 23.9 |
| 1 hr | 1.3 | 7.5 | 13.2 | 17.4 | 17.1 | 20.7 |
| 2 hr | 0.2 | 3.8 | 7.9 | 13.3 | 12.2 | 14.9 |

As shown in Table 4 above, among allulose epimerase variants in which one amino acid residue was substituted with another amino acid residue of the wild-type allulose epimerase derived from *Flavonifractor plautii*, the conversion activity of fructose to allulose of W29K, G216S, and M234I was almost the same as or higher than that of the wild type and showed significantly improved thermal stability regardless of heat treatment, compared to the wild type of allulose epimerase derived from *Flavonifractor plautii*. Further, among allulose epimerase variants in which two amino acid residues were substituted with other amino acid residues of the wild-type allulose epimerase derived from *Flavonifractor plautii*, the conversion activity of fructose to allulose of W29K/M234I had excellent conversion activity of fructose to allulose and thermal stability regardless of heat treatment. In addition, the allulose epimerase variant W29K/G216S/M234I in which three amino acid residues of the wild-type allulose epimerase derived from *Flavonifractor plautii* were substituted with other amino acid residues had the best conversion activity of fructose to allulose and thermal stability regardless of heat treatment.

As described above, the present invention has been described through the above embodiments, but the present invention is not necessarily limited thereto, and various modifications can be made without departing from the scope and spirit of the present invention. Accordingly, the scope of protection of the present invention should be construed as including all embodiments falling within the scope of the claims appended to the present invention.

The invention claimed is:

1. An allulose epimerase variant consisting of any one amino acid sequence selected from the amino acid sequence represented by SEQ ID NO: 2, the amino acid sequence represented by SEQ ID NO: 11, or the amino acid sequence represented by SEQ ID NO: 13.

2. A polynucleotide encoding the allulose epimerase variant of claim 1.

3. The polynucleotide of claim 2, wherein the polynucleotide consists of any one nucleotide sequence selected from the nucleotide sequence represented by SEQ ID NO: 15, the nucleotide sequence represented by SEQ ID NO: 24, or the nucleotide sequence represented by SEQ ID NO: 26.

4. A recombinant vector comprising the polynucleotide of claim 2.

5. A recombinant strain transformed by any one of the recombinant vectors of claim 4.

6. A method for preparing an allulose epimerase variant, the method comprising step of:
culturing the recombinant strain of claim 5 to express an allulose epimerase variant; and
isolating the allulose epimerase variant from a lysate of the recombinant strain expressing the allulose epimerase variant.

7. A composition for preparing allulose, the composition comprising the allulose epimerase variant of claim 1.

8. A composition for preparing allulose, the composition comprising: the recombinant strain of claim 5, a culture of the recombinant strain, or a lysate of the recombinant strain.

9. A method for preparing allulose, the method comprising reacting fructose with the allulose epimerase variant of claim 1 or a composition comprising the allulose epimerase variant.

10. A method for preparing allulose, the method comprising reacting fructose with the recombinant strain of claim 5, a culture of the recombinant strain, a lysate of the recombinant strain, or a composition comprising any one or more thereof.

* * * * *

SEQUENCE LISTING

```
<160> NUMBER OF SEQ ID NOS: 42

<210> SEQ ID NO 1
<211> LENGTH: 294
<212> TYPE: PRT
<213> ORGANISM: Unknown
<220> FEATURE:
<223> OTHER INFORMATION: Wild type D-allulose 3-epimerase derived from
      Flavonifractor plautii

<400> SEQUENCE: 1

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Ala Leu Lys Gln
225                 230                 235                 240

Val Asn Tyr Gln Gly Ala Ile Val Met Glu Pro Phe Val Leu Met Gly
                245                 250                 255
```

```
Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

<210> SEQ ID NO 2
<211> LENGTH: 294
<212> TYPE: PRT
<213> ORGANISM: Artificial Sequence
<220> FEATURE:
<223> OTHER INFORMATION: D-allulose 3-epimerase variant W29K

<400> SEQUENCE: 2

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

<210> SEQ ID NO 3
```

-continued

```
<211> LENGTH: 294
<212> TYPE: PRT
<213> ORGANISM: Artificial Sequence
<220> FEATURE:
<223> OTHER INFORMATION: D-allulose 3-epimerase variant C35L

<400> SEQUENCE: 3
```

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Leu Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

```
<210> SEQ ID NO 4
<211> LENGTH: 294
<212> TYPE: PRT
<213> ORGANISM: Artificial Sequence
<220> FEATURE:
<223> OTHER INFORMATION: D-allulose 3-epimerase variant D79P

<400> SEQUENCE: 4
```

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe

```
                20                  25                  30
Asp Ile Cys Glu Val Ala Ser Ala Glu Trp Gly Tyr Tyr Asp Asp Ala
            35                  40                  45
Arg Leu Arg Glu Leu Lys Ala Cys Ala Asp His Asn Gly Leu Gly Ile
        50                  55                  60
Thr Tyr Ser Ile Gly Leu Glu Ala Lys Tyr Asp Leu Ala Ser Pro Asp
65                  70                  75                  80
Pro Ala Val Arg Glu Asn Gly Ile Arg His Val Thr Arg Ile Leu Glu
                85                  90                  95
Ser Met Pro Lys Val Gly Ala Ala Ile Leu Asn Gly Val Ser Tyr Ala
            100                 105                 110
Gly Trp Gln Ala Leu Pro Asp His Gly Ile Thr Leu Asp Glu Lys Arg
        115                 120                 125
Arg Lys Glu Glu Leu Ala Leu Glu Ser Met Ser Arg Leu Met Lys Val
    130                 135                 140
Ala Glu Asp Cys Gly Val Leu Tyr Cys Cys Glu Val Val Asn Arg Phe
145                 150                 155                 160
Glu Gln Tyr Leu Leu Asn Thr Ala Lys Glu Gly Val Glu Phe Val Lys
                165                 170                 175
Arg Leu Gly Ser Pro Asn Ala Arg Val Leu Leu Asp Thr Phe His Met
            180                 185                 190
Asn Ile Glu Glu Asp Ser Met Val Asp Ala Ile Leu Glu Ala Gly Pro
        195                 200                 205
Trp Leu Gly His Phe His Val Gly Glu Asn Asn Arg Arg Pro Ala Gly
    210                 215                 220
Ser Thr Asn Arg Leu Pro Trp Lys Asp Met Ala Ala Ala Leu Lys Gln
225                 230                 235                 240
Val Asn Tyr Gln Gly Ala Ile Val Met Glu Pro Phe Val Leu Met Gly
                245                 250                 255
Gly Thr Ile Pro Tyr Asp Ile Lys Val Trp Arg Asp Leu Ser Gly Gly
            260                 265                 270
Ala Gly Glu Ala Gly Leu Asp Glu Met Ala Gly Arg Ala Cys Arg Phe
        275                 280                 285
Leu Lys Glu Leu Thr Ala
    290

<210> SEQ ID NO 5
<211> LENGTH: 294
<212> TYPE: PRT
<213> ORGANISM: Artificial Sequence
<220> FEATURE:
<223> OTHER INFORMATION: D-allulose 3-epimerase variant V109A

<400> SEQUENCE: 5

Met Asn Pro Ile Gly Met His Tyr Gly Phe Trp Ser His Asn Trp Asp
1               5                   10                  15
Glu Ile Ala Tyr Ile Pro Leu Met Glu Lys Leu Ala Trp Leu Gly Phe
                20                  25                  30
Asp Ile Cys Glu Val Ala Ser Ala Glu Trp Gly Tyr Tyr Asp Asp Ala
            35                  40                  45
Arg Leu Arg Glu Leu Lys Ala Cys Ala Asp His Asn Gly Leu Gly Ile
        50                  55                  60
Thr Tyr Ser Ile Gly Leu Glu Ala Lys Tyr Asp Leu Ala Ser Asp Asp
65                  70                  75                  80
Pro Ala Val Arg Glu Asn Gly Ile Arg His Val Thr Arg Ile Leu Glu
```

```
            85                  90                  95
Ser Met Pro Lys Val Gly Ala Ala Ile Leu Asn Gly Ala Ser Tyr Ala
            100                 105                 110

Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
            130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
            195                 200                 205

Trp Leu Gly His Phe His Val Gly Glu Asn Asn Arg Arg Pro Ala Gly
            210                 215                 220

Ser Thr Asn Arg Leu Pro Trp Lys Asp Met Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
            275                 280                 285

Leu Lys Glu Leu Thr Ala
            290

<210> SEQ ID NO 6
<211> LENGTH: 294
<212> TYPE: PRT
<213> ORGANISM: Artificial Sequence
<220> FEATURE:
<223> OTHER INFORMATION: D-allulose 3-epimerase variant M199F

<400> SEQUENCE: 6

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Cys Glu Val Ala Ser Ala Glu Trp Gly Tyr Tyr Asp Asp Ala
            35                  40                  45

Arg Leu Arg Glu Leu Lys Ala Cys Ala Asp His Asn Gly Leu Gly Ile
            50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
            130                 135                 140

Ala Glu Asp Cys Gly Val Leu Tyr Cys Cys Glu Val Val Asn Arg Phe
```

```
145                 150                 155                 160
Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Phe Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

<210> SEQ ID NO 7
<211> LENGTH: 294
<212> TYPE: PRT
<213> ORGANISM: Artificial Sequence
<220> FEATURE:
<223> OTHER INFORMATION: D-allulose 3-epimerase variant G216S

<400> SEQUENCE: 7

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
                20                  25                  30

Asp Ile Cys Glu Val Ala Ser Ala Glu Trp Gly Tyr Tyr Asp Asp Ala
            35                  40                  45

Arg Leu Arg Glu Leu Lys Ala Cys Ala Asp His Asn Gly Leu Gly Ile
        50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Ser Glu Asn Asn Arg Arg Pro Ala Gly
    210                 215                 220
```

Ser Thr Asn Arg Leu Pro Trp Lys Asp Met Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
                260                 265                 270

Ala Gly Glu Ala Gly Leu Asp Glu Met Ala Gly Arg Ala Cys Arg Phe
            275                 280                 285

Leu Lys Glu Leu Thr Ala
            290

<210> SEQ ID NO 8
<211> LENGTH: 294
<212> TYPE: PRT
<213> ORGANISM: Artificial Sequence
<220> FEATURE:
<223> OTHER INFORMATION: D-allulose 3-epimerase variant N218C

<400> SEQUENCE: 8

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
                20                  25                  30

Asp Ile Cys Glu Val Ala Ser Ala Glu Trp Gly Tyr Tyr Asp Asp Ala
            35                  40                  45

Arg Leu Arg Glu Leu Lys Ala Cys Ala Asp His Asn Gly Leu Gly Ile
50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
                100                 105                 110

Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
            195                 200                 205

Trp Leu Gly His Phe His Val Gly Glu Cys Asn Arg Arg Pro Ala Gly
            210                 215                 220

Ser Thr Asn Arg Leu Pro Trp Lys Asp Met Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
                260                 265                 270

Ala Gly Glu Ala Gly Leu Asp Glu Met Ala Gly Arg Ala Cys Arg Phe

Leu Lys Glu Leu Thr Ala
290

<210> SEQ ID NO 9
<211> LENGTH: 294
<212> TYPE: PRT
<213> ORGANISM: Artificial Sequence
<220> FEATURE:
<223> OTHER INFORMATION: D-allulose 3-epimerase variant M234I

<400> SEQUENCE: 9

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Ile Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
290

<210> SEQ ID NO 10
<211> LENGTH: 294
<212> TYPE: PRT
<213> ORGANISM: Artificial Sequence
<220> FEATURE:
<223> OTHER INFORMATION: D-allulose 3-epimerase variant W29K/G216S

<400> SEQUENCE: 10

```
Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Ser Glu Asn Asn Arg Arg Pro Ala Gly
    210                 215                 220

Ser Thr Asn Arg Leu Pro Trp Lys Asp Met Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290
```

<210> SEQ ID NO 11
<211> LENGTH: 294
<212> TYPE: PRT
<213> ORGANISM: Artificial Sequence
<220> FEATURE:
<223> OTHER INFORMATION: D-allulose 3-epimerase variant W29K/M234I

<400> SEQUENCE: 11

```
Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala
        35                  40                  45
```

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
 65                  70                  75                  80

Pro Ala Val Arg Glu Asn Gly Ile Arg His Val Thr Arg Ile Leu Glu
                 85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
            195                 200                 205

Trp Leu Gly His Phe His Val Gly Glu Asn Asn Arg Arg Pro Ala Gly
210                 215                 220

Ser Thr Asn Arg Leu Pro Trp Lys Asp Ile Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
            275                 280                 285

Leu Lys Glu Leu Thr Ala
    290

<210> SEQ ID NO 12
<211> LENGTH: 294
<212> TYPE: PRT
<213> ORGANISM: Artificial Sequence
<220> FEATURE:
<223> OTHER INFORMATION: D-allulose 3-epimerase variant G216S/M234I

<400> SEQUENCE: 12

Met Asn Pro Ile Gly Met His Tyr Gly Phe Trp Ser His Asn Trp Asp
 1               5                  10                  15

Glu Ile Ala Tyr Ile Pro Leu Met Glu Lys Leu Ala Trp Leu Gly Phe
             20                  25                  30

Asp Ile Cys Glu Val Ala Ser Ala Glu Trp Gly Tyr Tyr Asp Asp Ala
             35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
 65                  70                  75                  80

Pro Ala Val Arg Glu Asn Gly Ile Arg His Val Thr Arg Ile Leu Glu
                 85                  90                  95

Ser Met Pro Lys Val Gly Ala Ala Ile Leu Asn Gly Val Ser Tyr Ala
            100                 105                 110

```
Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Ser Glu Asn Asn Arg Arg Pro Ala Gly
    210                 215                 220

Ser Thr Asn Arg Leu Pro Trp Lys Asp Ile Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

<210> SEQ ID NO 13
<211> LENGTH: 294
<212> TYPE: PRT
<213> ORGANISM: Artificial Sequence
<220> FEATURE:
<223> OTHER INFORMATION: D-allulose 3-epimerase variant W29K/G216S/M234I

<400> SEQUENCE: 13

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175
```

```
Arg Leu Gly Ser Pro Asn Ala Arg Val Leu Asp Thr Phe His Met
            180                 185                 190
Asn Ile Glu Glu Asp Ser Met Val Asp Ala Ile Leu Glu Ala Gly Pro
        195                 200                 205
Trp Leu Gly His Phe His Val Ser Glu Asn Asn Arg Arg Pro Ala Gly
    210                 215                 220
Ser Thr Asn Arg Leu Pro Trp Lys Asp Ile Ala Ala Leu Lys Gln
225                 230                 235                 240
Val Asn Tyr Gln Gly Ala Ile Val Met Glu Pro Phe Val Leu Met Gly
                245                 250                 255
Gly Thr Ile Pro Tyr Asp Ile Lys Val Trp Arg Asp Leu Ser Gly Gly
            260                 265                 270
Ala Gly Glu Ala Gly Leu Asp Glu Met Ala Gly Arg Ala Cys Arg Phe
        275                 280                 285
Leu Lys Glu Leu Thr Ala
    290
```

```
<210> SEQ ID NO 14
<211> LENGTH: 885
<212> TYPE: DNA
<213> ORGANISM: Unknown
<220> FEATURE:
<223> OTHER INFORMATION: Polynucleotide coding wild type D-allulose
      3-epimerase derived from Flavonifractor plautii

<400> SEQUENCE: 14
atgaacccga ttggaatgca ctacggcttc tggagccaca actgggacga gattgcatac    60
atacccctga tggagaagct ggcctggctg ggctttgaca tctgcgaggt ggcctccgcc   120
gagtggggct attacgacga cgccaggctg cgggagctga aggcctgcgc cgatcacaac   180
ggcctgggca tcacctattc catcggcctg gaggccaaat acgacctggc cagcgacgat   240
ccggcggtgc gggagaacgg catccgccat gtcacccgca tcctggagag catgcccaag   300 gtggggcgg ccatcctcaa cggcgtgtcc tacgccgggt ggcaggccct gcccgaccac   360
ggaatcaccc tggacgagaa cgccgcaag gaggagcttg ccctggagtc catgtcccgg   420
ctcatgaagg tggcggagga ctgcggcgtg ctctactgct gcgaggtggt caaccgcttc   480
gagcagtacc tgctcaacac cgccaaagag ggcgtggagt ttgtcaagcg cctgggcagt   540
cccaacgccc gggtgctgct ggataccttc cacatgaaca tcgaggagga cagcatggtg   600
gacgccattc tggaggcggg cccctggctg ggcattttcc acgtggggga gaacaaccgc   660
cgccccgccg gctccaccaa ccgcctgccc tggaaggaca tggccgccgc cctcaagcag   720
gtgaactacc aggggccat tgtgatggag cccttcgtgc tcatgggggg taccattccc   780
tatgatatca aggtctggcg ggatctcagc ggcggggccg ggaggccgg gctggacgag   840 atggcgggcc gggcctgccg gttcctcaag gagctgaccg cgtaa              885
```

```
<210> SEQ ID NO 15
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K

<400> SEQUENCE: 15
atgaacccga ttggaatgca ctacggcttc tggagccaca actgggacga gattgcatac    60
atacccctga tggagaagct ggccaaactg ggctttgaca tctgcgaggt ggcctccgcc   120
```

```
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300
gtgggggcgg ccatcctcaa cggcgtgtcc tacgccgggt ggcaggccct gcccgaccac    360
ggaatcaccc tggacgagaa gcgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg gggcatttcc acgtggggga gaacaaccgc    660
cgccccgccg gctccaccaa ccgcctgccc tggaaggaca tggccgccgc cctcaagcag    720
gtgaactacc aggggggcat tgtgatggag cccttcgtgc tcatggggg taccattccc    780 tatgatatca aggtctggcg ggatctcagc ggcggggccg gggaggccgg gctggacgag    840
atggcgggcc gggcctgccg gttcctcaag gagctgaccg cgtaa              885

<210> SEQ ID NO 16
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant C35L

<400> SEQUENCE: 16
atgaacccga ttggaatgca ctacggcttc tggagccaca actgggacga gattgcatac     60 ataccctga tggagaagct ggcctggctg ggctttgaca tcctggaggt ggcctccgcc    120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300
gtgggggcgg ccatcctcaa cggcgtgtcc tacgccgggt ggcaggccct gcccgaccac    360
ggaatcaccc tggacgagaa gcgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg gggcatttcc acgtggggga gaacaaccgc    660
cgccccgccg gctccaccaa ccgcctgccc tggaaggaca tggccgccgc cctcaagcag    720
gtgaactacc aggggggcat tgtgatggag cccttcgtgc tcatggggg taccattccc    780 tatgatatca aggtctggcg ggatctcagc ggcggggccg gggaggccgg gctggacgag    840
atggcgggcc gggcctgccg gttcctcaag gagctgaccg cgtaa              885

<210> SEQ ID NO 17
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant D79P

<400> SEQUENCE: 17
```

```
atgaacccga ttggaatgca ctacggcttc tggagccaca actgggacga gattgcatac    60
atacccctga tggagaagct ggcctggctg ggctttgaca tctgcgaggt ggcctccgcc   120
gagtggggct attacgacga cgccaggctg cgggagctga aggcctgcgc cgatcacaac   180
ggcctgggca tcacctattc catcggcctg gaggccaaat acgacctggc cagccccgat   240
ccggcggtgc gggagaacgg catccgccat gtcacccgca tcctggagag catgcccaag   300 gtggggcgg  ccatcctcaa cggcgtgtcc tacgccgggt ggcaggccct gcccgaccac   360
ggaatcaccc tggacgagaa cgccgcaag  gaggagcttg ccctggagtc catgtcccgg   420
ctcatgaagg tggcggagga ctgcggcgtg ctctactgct gcgaggtggt caaccgcttc   480
gagcagtacc tgctcaacac cgccaaagag ggcgtggagt ttgtcaagcg cctgggcagt   540
cccaacgccc gggtgctgct ggataccttc cacatgaaca tcgaggagga cagcatggtg   600
gacgccattc tggaggcggg ccctggctg  gggcatttcc acgtggggga gaacaaccgc   660
cgccccgccg gctccaccaa ccgcctgccc tggaaggaca tggccgccgc cctcaagcag   720
gtgaactacc aggggggccat tgtgatggag cccttcgtgc tcatgggggg taccattccc   780
tatgatatca aggtctggcg ggatctcagc ggcggggccg gggaggccgg gctggacgag   840
atggcgggcc gggcctgccg gttcctcaag gagctgaccg cgtaa                   885
```

<210> SEQ ID NO 18
<211> LENGTH: 885
<212> TYPE: DNA
<213> ORGANISM: Artificial Sequence
<220> FEATURE:
<223> OTHER INFORMATION: Polynucleotide coding D-allulose 3-epimerase variant V109A

<400> SEQUENCE: 18

```
atgaacccga ttggaatgca ctacggcttc tggagccaca actgggacga gattgcatac    60
atacccctga tggagaagct ggcctggctg ggctttgaca tctgcgaggt ggcctccgcc   120
gagtggggct attacgacga cgccaggctg cgggagctga aggcctgcgc cgatcacaac   180
ggcctgggca tcacctattc catcggcctg gaggccaaat acgacctggc cagcgacgat   240
ccggcggtgc gggagaacgg catccgccat gtcacccgca tcctggagag catgcccaag   300 gtggggcgg  ccatcctcaa cggcgcctcc tacgccgggt ggcaggccct gcccgaccac   360
ggaatcaccc tggacgagaa cgccgcaag  gaggagcttg ccctggagtc catgtcccgg   420
ctcatgaagg tggcggagga ctgcggcgtg ctctactgct gcgaggtggt caaccgcttc   480
gagcagtacc tgctcaacac cgccaaagag ggcgtggagt ttgtcaagcg cctgggcagt   540
cccaacgccc gggtgctgct ggataccttc cacatgaaca tcgaggagga cagcatggtg   600
gacgccattc tggaggcggg ccctggctg  gggcatttcc acgtggggga gaacaaccgc   660
cgccccgccg gctccaccaa ccgcctgccc tggaaggaca tggccgccgc cctcaagcag   720
gtgaactacc aggggggccat tgtgatggag cccttcgtgc tcatgggggg taccattccc   780
tatgatatca aggtctggcg ggatctcagc ggcggggccg gggaggccgg gctggacgag   840
atggcgggcc gggcctgccg gttcctcaag gagctgaccg cgtaa                   885
```

<210> SEQ ID NO 19
<211> LENGTH: 885
<212> TYPE: DNA
<213> ORGANISM: Artificial Sequence
<220> FEATURE:
<223> OTHER INFORMATION: Polynucleotide coding D-allulose 3-epimerase variant M199F

<400> SEQUENCE: 19

```
atgaacccga ttggaatgca ctacggcttc tggagccaca actgggacga gattgcatac      60
ataccectga tggagaagct ggcctggctg gctttgaca tctgcgaggt ggcctccgcc      120
gagtggggct attacgacga cgccaggctg cgggagctga aggcctgcgc cgatcacaac      180
ggcctgggca tcacctattc catcggcctg gaggccaaat acgacctggc cagcgacgat      240
ccggcggtgc gggagaacgg catccgccat gtcacccgca tcctggagag catgcccaag      300
gtgggggcgg ccatcctcaa cggcgtgtcc tacgccgggt ggcaggccct gcccgaccac      360
ggaatcaccc tggacgagaa cgccgcaag gaggagcttg ccctggagtc catgtcccgg      420
ctcatgaagg tggcggagga ctgcggcgtg ctctactgct gcgaggtggt caaccgcttc      480
gagcagtacc tgctcaacac cgccaaagag ggcgtggagt ttgtcaagcg cctgggcagt      540
cccaacgccc gggtgctgct ggataccttc cacatgaaca tcgaggagga cagcttcgtg      600
gacgccattc tggaggcggg ccctggctg gggcatttcc acgtggggga gaacaaccgc      660
cgccccgccg gctccaccaa ccgcctgccc tggaaggaca tggccgccgc cctcaagcag      720
gtgaactacc aggggggccat tgtgatggag cccttcgtgc tcatgggggg taccattccc      780
tatgatatca aggtctggcg ggatctcagc ggcggggccg gggaggccgg gctggacgag      840
atggcgggcc gggcctgccg gttcctcaag gagctgaccg cgtaa                      885
```

<210> SEQ ID NO 20
<211> LENGTH: 885
<212> TYPE: DNA
<213> ORGANISM: Artificial Sequence
<220> FEATURE:
<223> OTHER INFORMATION: Polynucleotide coding D-allulose 3-epimerase variant G216S

<400> SEQUENCE: 20

```
atgaacccga ttggaatgca ctacggcttc tggagccaca actgggacga gattgcatac      60
ataccectga tggagaagct ggcctggctg gctttgaca tctgcgaggt ggcctccgcc      120
gagtggggct attacgacga cgccaggctg cgggagctga aggcctgcgc cgatcacaac      180
ggcctgggca tcacctattc catcggcctg gaggccaaat acgacctggc cagcgacgat      240
ccggcggtgc gggagaacgg catccgccat gtcacccgca tcctggagag catgcccaag      300
gtgggggcgg ccatcctcaa cggcgtgtcc tacgccgggt ggcaggccct gcccgaccac      360
ggaatcaccc tggacgagaa cgccgcaag gaggagcttg ccctggagtc catgtcccgg      420
ctcatgaagg tggcggagga ctgcggcgtg ctctactgct gcgaggtggt caaccgcttc      480
gagcagtacc tgctcaacac cgccaaagag ggcgtggagt ttgtcaagcg cctgggcagt      540
cccaacgccc gggtgctgct ggataccttc cacatgaaca tcgaggagga cagcatggtg      600
gacgccattc tggaggcggg ccctggctg gggcatttcc acgtgagcga gaacaaccgc      660
cgccccgccg gctccaccaa ccgcctgccc tggaaggaca tggccgccgc cctcaagcag      720
gtgaactacc aggggggccat tgtgatggag cccttcgtgc tcatgggggg taccattccc      780
tatgatatca aggtctggcg ggatctcagc ggcggggccg gggaggccgg gctggacgag      840
atggcgggcc gggcctgccg gttcctcaag gagctgaccg cgtaa                      885
```

<210> SEQ ID NO 21
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant N218C

<400> SEQUENCE: 21

| | | | | | | |
|---|---|---|---|---|---|---|
| atgaacccga | ttggaatgca | ctacggcttc | tggagccaca | actgggacga | gattgcatac | 60 |
| atacccctga | tggagaagct | ggcctggctg | ggctttgaca | tctgcgaggt | ggcctccgcc | 120 |
| gagtggggct | attacgacga | cgccaggctg | cgggagctga | aggcctgcgc | cgatcacaac | 180 |
| ggcctgggca | tcacctattc | catcggcctg | gaggccaaat | acgacctggc | cagcgacgat | 240 |
| ccggcggtgc | gggagaacgg | catccgccat | gtcacccgca | tcctggagag | catgcccaag | 300 |
| gtggggcgg | ccatcctcaa | cggcgtgtcc | tacgccgggt | ggcaggccct | gcccgaccac | 360 |
| ggaatcaccc | tggacgagaa | cgccgcaag | gaggagcttg | ccctggagtc | catgtcccgg | 420 |
| ctcatgaagg | tggcggagga | ctgcggcgtg | ctctactgct | gcgaggtggt | caaccgcttc | 480 |
| gagcagtacc | tgctcaacac | cgccaaagag | ggcgtggagt | ttgtcaagcg | cctgggcagt | 540 |
| cccaacgccc | gggtgctgct | ggataccttc | acatgaaca | tcgaggagga | cagcatggtg | 600 |
| gacgccattc | tggaggcggg | cccctggctg | gggcatttcc | acgtggggga | gtgcaaccgc | 660 |
| cgccccgccg | gctccaccaa | ccgcctgccc | tggaaggaca | tggccgccgc | cctcaagcag | 720 |
| gtgaactacc | aggggccat | tgtgatggag | cccttcgtgc | tcatgggggg | taccattccc | 780 |
| tatgatatca | aggtctggcg | ggatctcagc | ggcggggccg | gggaggccgg | gctggacgag | 840 |
| atggcgggcc | gggcctgccg | gttcctcaag | gagctgaccg | cgtaa | | 885 |

<210> SEQ ID NO 22
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant M234I

<400> SEQUENCE: 22

| | | | | | | |
|---|---|---|---|---|---|---|
| atgaacccga | ttggaatgca | ctacggcttc | tggagccaca | actgggacga | gattgcatac | 60 |
| atacccctga | tggagaagct | ggcctggctg | ggctttgaca | tctgcgaggt | ggcctccgcc | 120 |
| gagtggggct | attacgacga | cgccaggctg | cgggagctga | aggcctgcgc | cgatcacaac | 180 |
| ggcctgggca | tcacctattc | catcggcctg | gaggccaaat | acgacctggc | cagcgacgat | 240 |
| ccggcggtgc | gggagaacgg | catccgccat | gtcacccgca | tcctggagag | catgcccaag | 300 |
| gtggggcgg | ccatcctcaa | cggcgtgtcc | tacgccgggt | ggcaggccct | gcccgaccac | 360 |
| ggaatcaccc | tggacgagaa | cgccgcaag | gaggagcttg | ccctggagtc | catgtcccgg | 420 |
| ctcatgaagg | tggcggagga | ctgcggcgtg | ctctactgct | gcgaggtggt | caaccgcttc | 480 |
| gagcagtacc | tgctcaacac | cgccaaagag | ggcgtggagt | ttgtcaagcg | cctgggcagt | 540 |
| cccaacgccc | gggtgctgct | ggataccttc | acatgaaca | tcgaggagga | cagcatggtg | 600 |
| gacgccattc | tggaggcggg | cccctggctg | gggcatttcc | acgtggggga | gaacaaccgc | 660 |
| cgccccgccg | gctccaccaa | ccgcctgccc | tggaaggaca | ttgccgccgc | cctcaagcag | 720 |
| gtgaactacc | aggggccat | tgtgatggag | cccttcgtgc | tcatgggggg | taccattccc | 780 |
| tatgatatca | aggtctggcg | ggatctcagc | ggcggggccg | gggaggccgg | gctggacgag | 840 |
| atggcgggcc | gggcctgccg | gttcctcaag | gagctgaccg | cgtaa | | 885 |

<210> SEQ ID NO 23

```
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/G216S

<400> SEQUENCE: 23
atgaacccga ttggaatgca ctacggcttc tggagccaca actgggacga gattgcatac     60
atacccctga tggagaagct ggccaaactg ggctttgaca tctgcgaggt ggcctccgcc    120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300 gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg ggcatttcc acgtgagcga gaacaaccgc    660
cgccccgccg gctccaccaa ccgcctgccc tggaaggaca tggccgccgc cctcaagcag    720
gtgaactacc aggggccat tgtgatggag cccttcgtgc tcatggggg taccattccc    780 tatgatatca aggtctggcg ggatctcagc ggcggggccg gggaggccgg gctggacgag    840
atggcgggcc gggcctgccg gttcctcaag gagctgaccg cgtaa                    885

<210> SEQ ID NO 24
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/M234I

<400> SEQUENCE: 24
atgaacccga ttggaatgca ctacggcttc tggagccaca actgggacga gattgcatac     60
atacccctga tggagaagct ggccaaactg ggctttgaca tctgcgaggt ggcctccgcc    120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300 gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg ggcatttcc acgtggggga gaacaaccgc    660
cgccccgccg gctccaccaa ccgcctgccc tggaaggaca ttgccgccgc cctcaagcag    720
gtgaactacc aggggccat tgtgatggag cccttcgtgc tcatggggg taccattccc    780 tatgatatca aggtctggcg ggatctcagc ggcggggccg gggaggccgg gctggacgag    840
atggcgggcc gggcctgccg gttcctcaag gagctgaccg cgtaa                    885
```

<210> SEQ ID NO 25
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant G216S/M234I

<400> SEQUENCE: 25

```
atgaacccga ttggaatgca ctacggcttc tggagccaca actgggacga gattgcatac      60 ataccccctga tggagaagct ggcctggctg ggctttgaca tctgcgaggt ggcctccgcc    120
gagtggggct attacgacga cgccaggctg cgggagctga aggcctgcgc cgatcacaac     180
ggcctgggca tcacctattc catcggcctg gaggccaaat acgacctggc cagcgacgat    240
ccggcggtgc gggagaacgg catccgccat gtcacccgca tcctggagag catgcccaag    300 gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg gggcatttcc acgtgagcga gaacaaccgc    660
cgccccgccg gctccaccaa ccgcctgccc tggaaggaca ttgccgccgc cctcaagcag    720
gtgaactacc aggggccat tgtgatggag cccttcgtgc tcatgggggg taccattccc    780
tatgatatca aggtctggcg ggatctcagc ggcggggccg gggaggccgg gctggacgag    840
atggcgggcc gggcctgccg gttcctcaag gagctgaccg cgtaa                    885
```

<210> SEQ ID NO 26
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/G216S/M234I

<400> SEQUENCE: 26

```
atgaacccga ttggaatgca ctacggcttc tggagccaca actgggacga gattgcatac     60 ataccccctga tggagaagct ggccaaactg ggctttgaca tctgcgaggt ggcctccgcc   120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300 gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg gggcatttcc acgtgagcga gaacaaccgc    660
cgccccgccg gctccaccaa ccgcctgccc tggaaggaca ttgccgccgc cctcaagcag    720
gtgaactacc aggggccat tgtgatggag cccttcgtgc tcatgggggg taccattccc    780
```

```
tatgatatca aggtctggcg ggatctcagc ggcggggccg gggaggccgg gctggacgag      840
atggcgggcc gggcctgccg gttcctcaag gagctgaccg cgtaa                     885
```

<210> SEQ ID NO 27
<211> LENGTH: 43
<212> TYPE: DNA
<213> ORGANISM: artificial sequence
<220> FEATURE:
<223> OTHER INFORMATION: synthetic sequence, W29K forward primer

<400> SEQUENCE: 27

```
ccctgatgga aagctggcc aaactgggct tgacatctg cga                         43
```

<210> SEQ ID NO 28
<211> LENGTH: 43
<212> TYPE: DNA
<213> ORGANISM: artificial sequence
<220> FEATURE:
<223> OTHER INFORMATION: synthetic sequence, WK29K reverse primer

<400> SEQUENCE: 28

```
tcgcagatgt caaagcccag tttggccagc ttctccatca ggg                       43
```

<210> SEQ ID NO 29
<211> LENGTH: 43
<212> TYPE: DNA
<213> ORGANISM: artificial sequence
<220> FEATURE:
<223> OTHER INFORMATION: synthetic sequence, G216S forward primer

<400> SEQUENCE: 29

```
ggctggggca tttccacgtg agcgagaaca accgccgccc cgc                       43
```

<210> SEQ ID NO 30
<211> LENGTH: 43
<212> TYPE: DNA
<213> ORGANISM: artificial sequence
<220> FEATURE:
<223> OTHER INFORMATION: synthetic sequence, G216S, reverse primer

<400> SEQUENCE: 30

```
gcggggcggc ggttgttctc gctcacgtgg aaatgcccca gcc                       43
```

<210> SEQ ID NO 31
<211> LENGTH: 43
<212> TYPE: DNA
<213> ORGANISM: artificial sequence
<220> FEATURE:
<223> OTHER INFORMATION: synthetic sequence, M234I forward primer

<400> SEQUENCE: 31

```
accgcctgcc ctggaaggac attgccgccg ccctcaagca ggt                       43
```

<210> SEQ ID NO 32
<211> LENGTH: 43
<212> TYPE: DNA
<213> ORGANISM: artificial sequence
<220> FEATURE:
<223> OTHER INFORMATION: synthetic sequence, M234I reverse primer

<400> SEQUENCE: 32

```
acctgcttga gggcggcggc aatgtccttc cagggcaggc ggt                       43
```

<210> SEQ ID NO 33
<211> LENGTH: 43

```
<212> TYPE: DNA
<213> ORGANISM: artificial sequence
<220> FEATURE:
<223> OTHER INFORMATION: synthetic sequence, C35L forward primer

<400> SEQUENCE: 33
cctggctggg ctttgacatc ctggaggtgg cctccgccga gtg                43

<210> SEQ ID NO 34
<211> LENGTH: 43
<212> TYPE: DNA
<213> ORGANISM: artificial sequence
<220> FEATURE:
<223> OTHER INFORMATION: synthetic sequence, C35L reverse primer

<400> SEQUENCE: 34
cactcggcgg aggccacctc caggatgtca aagcccagcc agg                43

<210> SEQ ID NO 35
<211> LENGTH: 43
<212> TYPE: DNA
<213> ORGANISM: artificial sequence
<220> FEATURE:
<223> OTHER INFORMATION: synthetic sequence, D79P forward primer

<400> SEQUENCE: 35
ccaaatacga cctggccagc cccgatccgg cggtgcggga gaa                43

<210> SEQ ID NO 36
<211> LENGTH: 43
<212> TYPE: DNA
<213> ORGANISM: artificial sequence
<220> FEATURE:
<223> OTHER INFORMATION: synthetic sequence, D79P reverse primer

<400> SEQUENCE: 36
ttctcccgca ccgccggatc ggggctggcc aggtcgtatt tgg                43

<210> SEQ ID NO 37
<211> LENGTH: 43
<212> TYPE: DNA
<213> ORGANISM: artificial sequence
<220> FEATURE:
<223> OTHER INFORMATION: synthetic sequence, V109A forward primer

<400> SEQUENCE: 37
gggcggccat cctcaacggc gcctcctacg ccgggtggca ggc                43

<210> SEQ ID NO 38
<211> LENGTH: 43
<212> TYPE: DNA
<213> ORGANISM: artificial sequence
<220> FEATURE:
<223> OTHER INFORMATION: synthetic sequence, V109A reverse primer

<400> SEQUENCE: 38
gcctgccacc cggcgtagga ggcgccgttg aggatggccg ccc                43

<210> SEQ ID NO 39
<211> LENGTH: 43
<212> TYPE: DNA
<213> ORGANISM: artificial sequence
<220> FEATURE:
<223> OTHER INFORMATION: synthetic sequence, M119F forward primer

<400> SEQUENCE: 39
```

```
tgaacatcga ggaggacagc ttcgtggacg ccattctgga ggc                           43

<210> SEQ ID NO 40
<211> LENGTH: 43
<212> TYPE: DNA
<213> ORGANISM: artificial sequence
<220> FEATURE:
<223> OTHER INFORMATION: syntetic sequence, M199F reverse primer

<400> SEQUENCE: 40
gcctccagaa tggcgtccac gaagctgtcc tcctcgatgt tca                           43

<210> SEQ ID NO 41
<211> LENGTH: 43
<212> TYPE: DNA
<213> ORGANISM: artificial sequence
<220> FEATURE:
<223> OTHER INFORMATION: synthetic sequence, N218C forward primer

<400> SEQUENCE: 41
ggcatttcca cgtgggggag tgcaaccgcc gccccgccgg ctc                           43

<210> SEQ ID NO 42
<211> LENGTH: 43
<212> TYPE: DNA
<213> ORGANISM: artificial sequence
<220> FEATURE:
<223> OTHER INFORMATION: synthetic sequence, N218C reverse primer

<400> SEQUENCE: 42
gagccggcgg ggcggcggtt gcactccccc acgtggaaat gcc                           43
```